United States Patent [19]

Brown

[11] Patent Number: 4,660,583

[45] Date of Patent: Apr. 28, 1987

[54] INTERDENTAL STIMULATOR

[75] Inventor: Frank P. Brown, Toronto, Canada

[73] Assignee: Kleen-Piks Inc., Downsview, Canada

[21] Appl. No.: 630,146

[22] Filed: Jul. 12, 1984

[30] Foreign Application Priority Data

Jul. 11, 1984 [CA] Canada .................................. 458,686

[51] Int. Cl.⁴ ............................................. A61C 15/00
[52] U.S. Cl. .................................... 132/89; 128/62 A
[58] Field of Search .................. 132/89, 93; 128/62 A

[56] References Cited

U.S. PATENT DOCUMENTS

| 2,008,206 | 7/1935 | Grant | 132/89 |
| 3,563,253 | 2/1971 | Barman | 132/89 |
| 3,672,378 | 6/1972 | Silverman | 132/93 |
| 3,978,872 | 9/1976 | Bond | 132/89 |
| 4,271,854 | 6/1981 | Bengtsson | 132/89 |

Primary Examiner—Robert P. Swiatek
Attorney, Agent, or Firm—Rogers, Bereskin & Parr

[57] ABSTRACT

An interdental stimulator is formed from an elongate member of generally triangular section. It has two end portions that taper down to respective ends of small cross-section. This enables either end portion to be used to clean interdental spaced and invigorate gums. The end portions have different height to width ratios, to accommodate different shaped interdental spaces.

29 Claims, 10 Drawing Figures

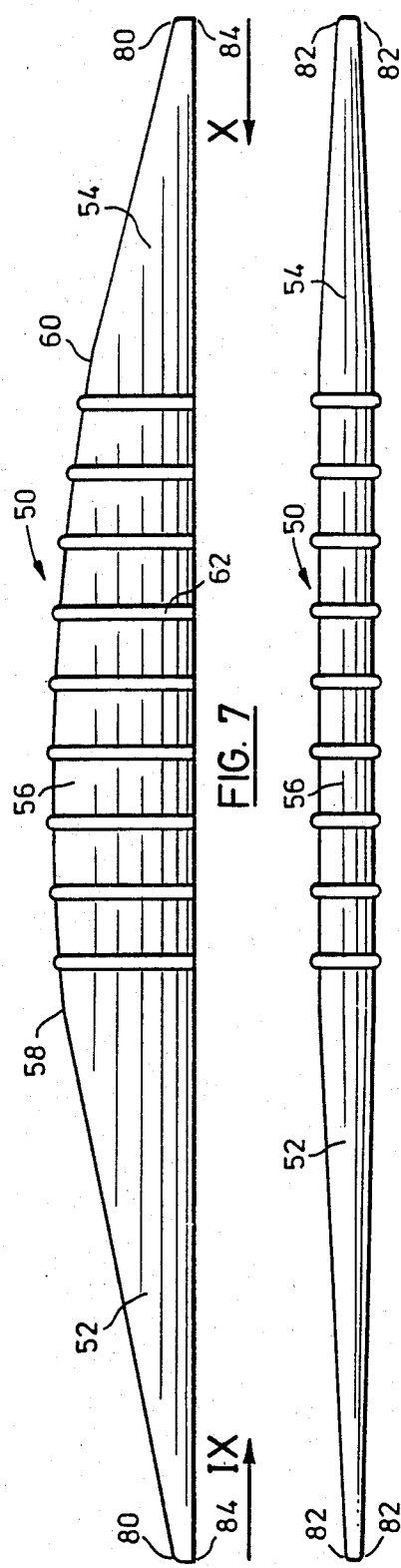
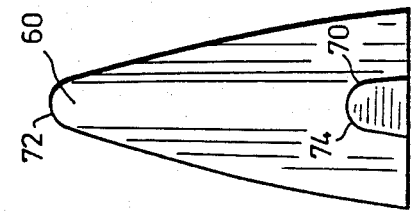
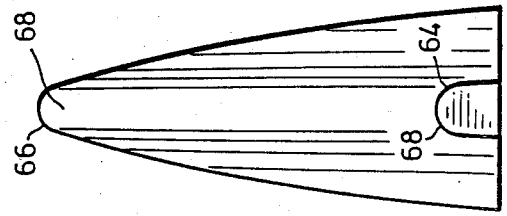
FIG. 7
FIG. 8
FIG. 9
FIG. 10

INTERDENTAL STIMULATOR

This invention relates to an interdental stimulator.

It has been recognized and known for some time that good dental care requires more than just regular brushing of the teeth. It is also desirable to clean the spaces between the teeth, and to ensure that the gums are cleaned and invigorated.

For this purpose, an interdental stimulator has been marketed under the name STIM.U.DENT (Registered Trade Mark) for over 40 years. This product comprises a small strip of soft wood of narrow triangular cross-section. One end, as viewed from the side tapers to a point and has a rounded top surface. The directions for this product state that this end, after moistening in the mouth should be inserted between the teeth against the gums. A narrow flat bottom surface contacts the gums, and the two longer sloped sides contact the teeth. By means of an in and out motion, it is stated that the teeth can be cleaned and the gums invigorated.

Whilst this product assists in cleaning teeth and invigorating gums, it has disadvantages. It is only manufactured in one profile, and only one end is shaped for use on a person's teeth and gums. However, the interdental spaces can be of a variety of different profiles. For very narrow spaces between teeth, this stimulator cannot reach up to a narrow upper portion of the space. Also, for spaces which are wide with less steeply sloping sides, the base of the stimulator is not wide enough to contact all the gum area, and because of its narrow profile it cannot reach the portions of the gum at the edges of the space. Consequently, those large portions of the gum cannot be invigorated, and cleaned.

According to the present invention, there is provided an interdental stimulator comprising an elongate member for insertion between adjacent teeth, the elongate member having a generally triangular profile and having first and second end portions, which taper down to respective first and second ends of small cross-section, with the first end portion having a height to width ratio greater than the height to width ratio of the second end portion.

The dental stimulator of the present invention thus provides a stimulator having two end portions of different profiles. This enables interdental spaces to be cleaned and the gums to be more invigorated more effectively. In use, the two ends can be used in either order. However, it is expected that, in use, the second end will be used initially. After insertion into an interdental space, the second end portion will be gently moved in and out, to massage and invigorate the full width of the gum adjacent the opening. Simultaneously, the edges of the teeth at the lower end of the opening will be cleaned. Then, the first end portion will be inserted, and if desired, this can be held up against the teeth. Again, it will be moved in and out, gently, to clean the edges of the teeth at the top of the opening between the teeth. By this means, all of the edge surfaces of the teeth can be cleaned, and the gums can be properly invigorated.

It is anticipated that the interdental stimulator of the present invention should be particularly suitable for use after dental work, such as restoration work, crowns, bridges etc., and also during post-surgical rehabilitation. The provision of two ends of different profiles makes it easier for the user to properly clean the teeth and stimulate the gums. Also, proper use of the stimulator can prevent plaque build-up, and remove particles of food etc from between the teeth. In this respect, it is to be noted that the soft gum tissue between the teeth cannot always be reached by flossing.

A further advantage of the stimulator of the present invention is that greater use can be made of each stimulator. Experience with known stimulators suggests that, where they are made from soft wood, the single end provided can become damaged before all the teeth have been cleaned, so that it is difficult to use for the last interdental spaces cleaned. As the present invention provides a stimulator with two useable end portions, it should be adequate for cleaning all the teeth at one time.

The present invention also provides a set of interdental stimulators, the set comprising a plurality of interdental stimulators as defined above, which are arranged side by side in a row, with central portions of the interdental stimulators contacting and being continuous with one another along lower side edges thereof.

Each set conveniently includes 20-30 stimulators, and is individually packaged, for distribution and sale.

The present invention further provides a method of forming an interdental stimulator as defined above, the method comprising: passing a first cutter having a first profile corresponding to the first end portion along an elongate member and along a first path such as to form the tapered profile for the first end portion of the elongate member; and passing a second cutter having a second profile corresponding to the second end portion of the elongate member and along a second path such as to form the tapered profile for the second end portion.

This technique can be applied to a set of stimulators, and in this case, the first cutter is of a depth such as to form narrow connecting strips extending between adjacent lower side edges of central portions of the interdental stimulators. Also, the second cutter is preferably passed along the central portion and moved away from the stimulator as it passes therealong, to form a curved step extending at least part way along the central portion.

The interdental stimulator can be formed from a variety of materials, but wood and a plastic, such as low density polyethylene, are preferred.

The method of forming an interdental stimulator as described above is particularly suited to wooden stimulators formed in sets. Also, as wood relatively rapidly becomes soft and worn in use, each end portion preferably has a convex upper edge or ridge, as viewed from the side, to help maintain a desired profile in use.

If plastic is used, the stimulators are preferably moulded in batches. They can be arranged side by side in mould, designed to form, for example, 100 stimulators. A variety of different gating arrangements can be included, to supply plastic to the mould cavities.

For both wood and plastic, the stimulators can be flavoured, with, for example, mint or menthol.

For a better understanding of the present invention, and to show more clearly how it may be carried into effect, reference will now be made, by way of example, to the accompanying drawings, which show a preferred embodiment of the present invention, and in which:

FIG. 7 shows a side view of an alternative embodiment of the stimulator;

FIG. 8 shows a plan view of the stimulator of FIG. 7;

FIG. 9 shows a view in the direction of arrow IX of FIG. 7; and

FIG. 10 shows a view in the direction of arrow X of FIG. 7.

Each interdental stimulator is generally denoted by the reference 1, and comprises a first end portion 4, a second end portion 6 and a central portion 8.

Figure 2:
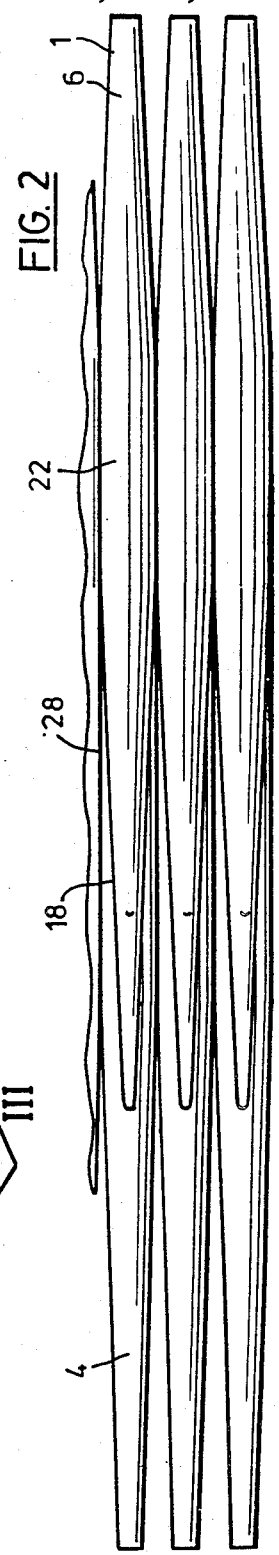
FIG. 2 shows a plan view of some of the stimulators of FIG. 1.
Figure 3:
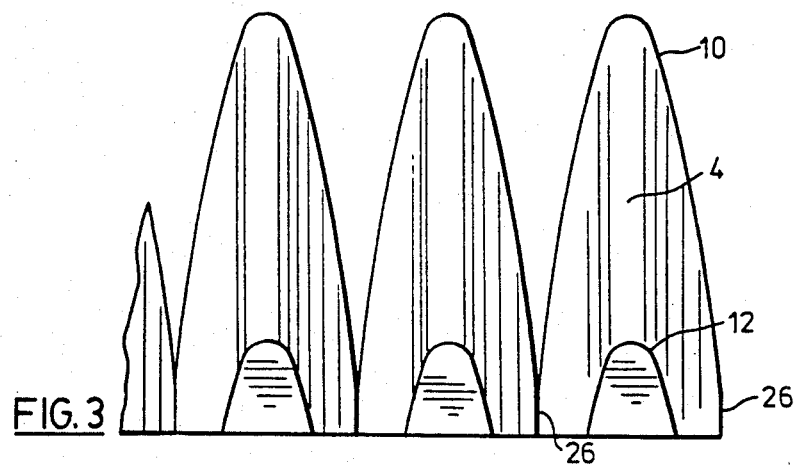
FIG. 3 shows a view in the direction of the arrows III in FIG. 1.

As shown in FIG. 3, the first end portion 4 has the profile 10, at the junction with the central portion 8, as indicted at 10a in FIG. 2. It tapers down to a profile 12, shown in FIG. 3, at the end 12a, indicated in FIG. 2. The profile 12 generally corresponds to the upper part of the larger profile 10, and these two profiles 10, 12 are determined by the cutter shape used to form the stimulator 1, as is described in greater detail below.

Figure 6:
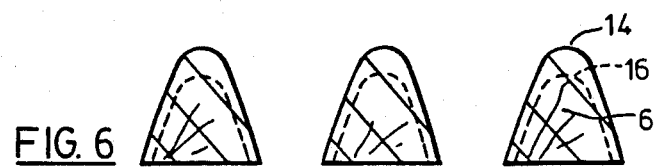
FIG. 6 shows a cross-sectional in the direction of arrows VI in FIG. 1.

The second end portion 6 has the profile 14 at the junction 14a between it and the central portion 8. At its free end, it tapers down to the section or profile 16, indicated at 16a at FIG. 2, the profiles 14, 16 being shown in FIG. 6.

The central portion 8 is a composite of 3 separate sections 18, 20 and 22. The section 18 is continuous with the first end portion 4, and has the profile 10, shown in FIG. 3. The section 22 is continuous with the second end portion 6, and has the profile 14, shown in FIG. 6. The central section 20, serves as a transitional section between the two outer portions 18, 22. The profile of this central section 20 is a combination of the two profiles 10, 14, as will become clear in the following description of manufacture. A step or very slight ridge 24 is formed between the two profiles. In this section 20, below the step or ridge 24, the profile corresponds to that of the profile 10 shown in FIG. 3. Above the step or ridge 24, the profile corresponds to the profile 14 shown in FIG. 6.

Figure 4:
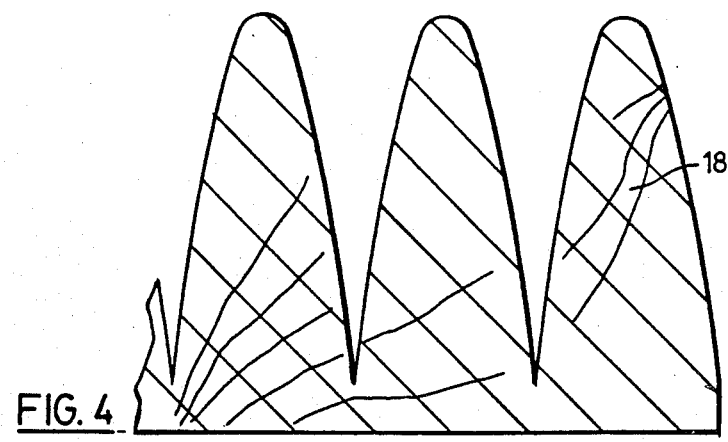
FIG. 4 shows a cross-sectional view in the direction of the arrows IV of FIG. 1.
Figure 5:
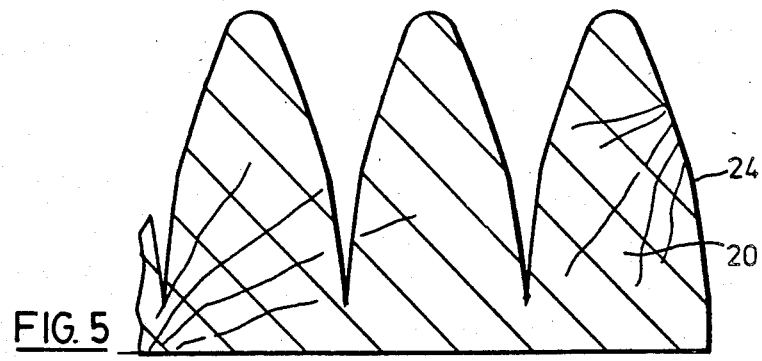
FIG. 5 shows a cross-sectional in the direction of arrows V in FIG. 1.

As shown in both FIGS. 3 and 4, both the profiles 10, 14 are provided with flat and vertical lower side surfaces indicated at 26, which extend upwards as far as a line 28. These side faces 26 provide connecting portions for the stimulator 1. It is cut, so that the side faces 26 are continuous with the side faces 26 of adjacent stimulators 1. This then provides a connection between adjacent stimulators 1. These lower side faces fall away at either end, at the beginning of the end portions 4, 6. This is indicated by line portions 30, 32 in FIG. 1. The slope of the lines 30, 32 corresponds to the slope of the top surface of the respective end portion, as viewed in FIG. 2.

Figure 1:
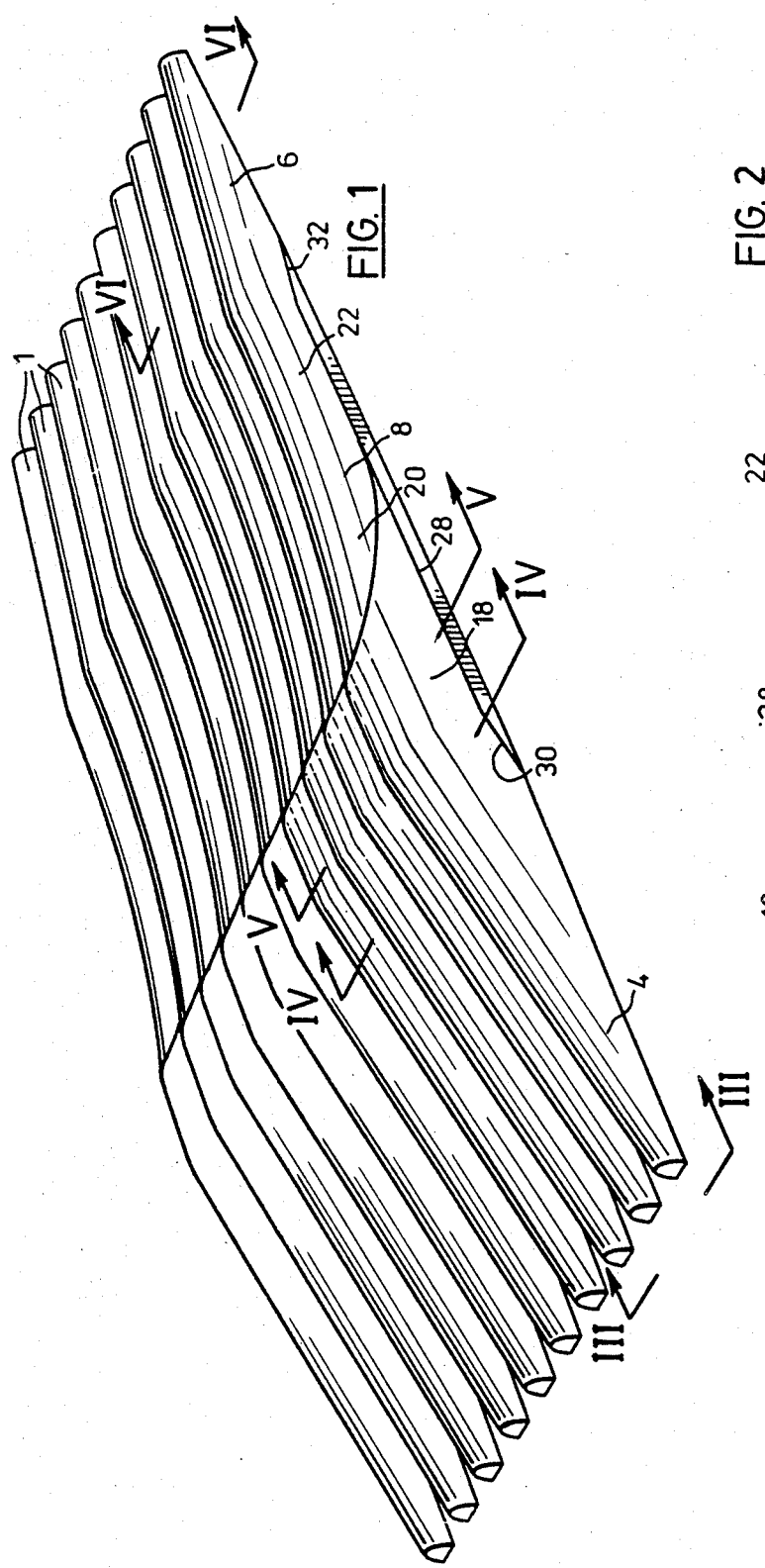
FIG. 1 shows a perspective view of a set of stimulators according to the present invention.

To form the stimulators, shown in FIG. 1, two rotary cutters are provided. Each of which is adapted to cut a batch or set of stimulators 1 simultaneously. For this purpose, each cutter effectively comprises a series of annular cutting elements arranged in a row along a shaft. The cutting elements are either formed individually and mounted on the shaft, or formed as a unitary body. Each cutting element forms the side of one stimulator, and the facing side of an adjacent stimulator. Each cutting element has for the first end portion 4, a radial depth corresponding to the depth of the profile 10 from its tip to the line 28. In other words, the cutter does not cut below the line 28. In use, the cutter is caused to follow a path, by means of a cam or the like, to form the required profile. Thus, the cutter will start off relatively low down, corresponding to the height of the profile 12. It will then travel along a ramp, corresponding to the slope of the first end portion 4. At the end of the ramp, it will travel in a horizontal straight line until the start of the second end portion 6, thereby forming the connecting side faces 26. It is to be borne in mind, that, at the beginning of the second end portion 6, the radially inner surfaces of the first cutter corresponding to the peak of the profile 10, will be spaced up above the top of the final profile of the stimulator 1, corresponding to the profile 10. The cutter 1 is then brought down a ramp sufficient to form the line 32. It can then be run out straight and horizontal along the rest of the second end portion 6. The exact path taken by the first cutter is immaterial at this point, provided it leaves enough material for the second cutter.

The second cutter is then traversed along the length of the batch or group of stimulators 1. The second cutter starts at the beginning of the central section 20. It is provided with a cam or the like, which causes it to follow a path corresponding to the upper surface of the central section 20, the section 22 and the end portion 6. Thus, the second cutter first follows a curved path corresponding to the top surface of the section 20. As it progresses along the section 20, it cuts deeper into the material, until it is fully engaged to the depth indicated by the line 28. The line 24 indicates the progressive engagement of the second cutter with the material. Traversing the section 22, the second cutter moves straight and horizontal. To form the end portion 6, the second cutter follows and inclined path corresponding to the top surface of the end portion 6. The curved top ridge of the central section 20 can correspond to the curvature of the second cutter.

Thus, each batch or set of dental stimulators 1 is formed by traversing a first cutter along the length of all the stimulators 1, and then traversing a second cutter along part of the length. It is also to be noted that the order of application of the cutters is immaterial; the second cutter could be employed first.

Whilst the dental stimulator 1 shows one profile, it is to be appreciated that a wide variety of profiles could be adopted. Below, details are given of the particular dimensions of the profile shown, and details of possible variations.

The dental stimulator 1 shown has an overall length of 55 mm and a width at its base of 2 mm. The end portion 4 is 20 mm long, and the end portion 6 is 12 mm long. The lengths of the sections 18, 20 and 22 of the central portion 18 are respectively 3 mm, 12 mm and 8 mm.

The profile 10 of the first end portion 4 has curved convex sides. These sides have a radius of 20 mm. The tip of the profile 10 has a radius of 0.25 mm At its base, its width corresponds to that of the stimulator 1 and is 2 mm. The profile 12, as noted above, corresponds to the profile 10, and at its base has a width of 0.9 mm. The height of the profile 10 is 4.5 mm, whilst the height of the profile 12 is 1 mm.

Turning to the profiles 6, 16 for the second end portion 6, these again have curved convex sides. Here again, the sides have a radius of 20 mm, and the radius at the tip is also again 0.25 mm. The larger profile 14 has a height of 3 mm, whilst the profile 16 has a height of 1 mm. The profile 16 also has a width of 1.12 mm. It is to be noted that the centres for the curved sides are lower than the centres for the profile 10, to give a small height to width ratio.

The height of the side faces 26, shown by the line 28, is 0.5 mm. The curved top surface of the central section 20 has a radius of 2½" or 63.5 mm.

The above dimensions are given for the particular dental stimulator 1 shown. A wide variety of possible alternative dimensions and profiles can be employed. In particular, for particular uses, it may be desirable to adopt profiles other than those shown. It is anticipated that the first end portion could have a length in the range 10–13 mm, and its maximum height could vary in the range 3–6.5 mm. Within these two sets of ranges, there is a wide variety of ranges for the slope of its top surface. Further, the tip, indicated by the profile 12, could have a height in the range 0.4–1.5 mm, with corresponding variations in the width. The radius of the side faces of the end portion 4 could vary in the range 10–30 mm.

Like the first end portion 4, the radius for the side faces of the second end portion 6 can vary and can have a radius in the range 10–40 mm. The height of the second end portion 6 can vary in the range 1.5–5.5 mm, and the height at the end indicated by the profile 16 can vary in the range 0.4–1.5 mm. The length of the second end portion can vary in the range 6–20 mm. Again, this will give a wide variety of angles for the top surface of the end portion 6.

The overall length of the stimulator can vary in the range 45–75 mm, and the width can vary in the range 1.2–3.5 mm.

The preferred material for the stimulator 1 is white pine or bass. To form the stimulators 1 in batches or sets, they are preferably cut continuously from a continuous strip of wood having a thickness corresponding to the height of the stimulators, this being 4.5 mm in this instance. The strip of wood should have a width corresponding to the length of the stimulators, in this case 55 mm, and the grain of the wood should extend across it. Then, the strip of wood can be continuously fed to the cutters, which are sequentially operated to cut out batches of stimulators.

Although wood is a preferred material, other materials, and in particular plastic, could be used. The principal requirement is that the material should be stiff enough to provide the required cleaning and invigorating action, whilst being sufficiently soft and resilient not to damage the teeth or gums.

It is also to be appreciated that the profile of the top of the end portions 4, 6, as viewed in FIG. 2, could have a variety of different profiles. Convex or other profiles are also possible, such as a profile formed by two straight lines at an obtuse angle. Convex profiles have advantages when applied to wood. Wood is soft, and, in use after wetting, can rapidly wear to an inconvenient concave profile. A convex profile should enable each end to have a longer life.

In use, a batch of stimulators 1, as shown in FIG. 1, would be supplied. Typically, they will come in a protective package, for protection and for hygiene reasons. A user then breaks off one stimulator 1, from one side of the set of batch of stimulators. As the stimulators are only connected by the shallow lower side faces 26 with a height of 0.5 mm, this can be accomplished easily. Then, one end portion is used in an interdental space. It is expected, that usually, the second end portion 6 will be used initially. This is broader and flatter than the other end portion, and should clean surfaces of the teeth adjacent the gum, whilst simultaneously cleaning and invigorating the width of the gum surface adjacent the space. For larger interdental spaces, the user could insert the stimulator so far as to use the section 22, having a profile corresponding to the largest profile of the end section 6. Once this operation has been satisfactorily completed, the user will switch to the other end portion 4. This is narrower and higher, and will clean teeth surfaces away from the gum and towards the top of the interdental space. Thus, use of both end portions should enable interdental spaces to be thoroughly cleaned and gums invigorated. This description of the sequence in use is only exemplary, and it is to be appreciated that the stimulator could be used in a variety of different ways. Thus, for example, one end portion could be applied to all the interdental spaces, before switching to the other one.

Reference will now be made to FIGS. 7–10, which show a second or alternative embodiment of the present invention. This embodiment of the interdental stimulator is designated by the reference 50. This embodiment of the toothpick pick 50 is shown by itself, as it is intended to be moulded in a plastic, such as low density polyethylene. In practice, it is expected that it will be most convenient and economical to mould batches of, for example, one hundred of these stimulators at once. The stimulators would be arranged side by side in a row, but separate from one another, in a mould. Various gate arragements could be used. For exmple gates can be provided at ends of the stimulator or at the middle. After noulding, the stimulators would be packaged loose.

A variety of different plastics can be used. The plastic can be soft or hard. It xay be desirable to provide the stimulators in two or more different types of plastic to give a user a choice of hardness. Also, each pack of stimulators could include a selection of stimulators of different hardness, and these could be colour coded for easy identification.

Like the first embodiment, the stimulator 50 has two ends, here designated 52, 54. As shown in FIG. 7, both the end portions 52, 54 have straight top surfaces. The plastic used is naturally resilient, and is not softened further when wetted in use. Consequently, it does not suffer from the wear difficulties of wood. Therefore, there is no need to provide a convex top surface, as suggested for the first, wooden embodiment, although a convex surface could be included.

Between the first and second end portions 52, 54, there is a central portion 56. The central portion 56 provides a transition between the maximum profile 58 of the first end portion 52, and the somewhat lower maximum profile 60 of the second end portion 54. It has a slight convex top surface, as shown in FIG. 7. Additionally, it is provided with a series of ribs, running around all sides, except for the bottom of the stimulator 50. These ribs are designated by the reference 62, The ribs 62 are of semi-circular cross-section, and are intended to aid gripping of the stimulator 50. If desired, they can be omitted, to give a smooth finish, comparable to that of the embodiment discussed above.

In particular, it is to be noted that, although this embodiment is primarily intended for moulding in plastic, it could be formed in wood. When wood is used, it is preferred that the ribs 62 are omitted, and the stimulators 50 can then be formed in batches, by the technique described for the first embodiment.

In the embodiment shown, there are nine ribs 62, but the number of ribs can be varied as desired, also the profile of the ribs can be altered. In particular, the ribs 62 could be given a lower or flatter profile, and their top portion omitted to enable a stimulator 50 to be more readily released from a mould.

FIG. 9 shows the maximum profile 58 of the first end portion 52, together with the minimum profile 64. (Strictly, the highest profile of the middle portion 56 should be shown, but this is omitted for clarity). Like the first portion 4 of the first embodiment, this first portion 52 has a relatively large height to width ratio. Like the first embodiment, the sides of the profile 58 have a radius of 20 mm, and the tip, indicated at 66, has a radius of 0.25 mm. The minimum profile 64 also has sides with a radius of 20 mm, and its tip 68 has a radius of 0.25 mm. Note that the centers for the sides of this profile 64 are somewhat higher than the centers for the corresponding sides of the profile 12, so that the sides are steeper in this embodiment at the tip. The height of the maximum profile 58 is 4.675 mm, and its width is 2 mm.

With reference to FIG. 10, the second end portion 54 has the maximum profile 60, and at its tip a minimum profile 70. Like the second end portion 6 of the first embodiment, and the first end portion 52, the sides of the profile 60 have a radius of 20 mm. Its tip, indicated at 72 has a radius of 0.25 mm. The minimum profile 70 similarly has sides with a radius of 20 mm, and a tip, indicated at 74, with a radius of 0.25 mm. Again, like the minimum profile 68, the centers for the curved sides are positioned relatively high, to give steep sides. The width of the maximum profile 60 is again 2 mm, whilst its height is 3.675 mm. The width of the minimum profile 70 is 0.6 mm, ie. slightly wider than the minimum profile 64 at the other end.

With regard to the general overall dimensions of this stimulator 50, the first end portion is 20 mm long. The second end portion 54 is 12 mm long, and the central portion 56 is 23 mm long, giving an overall length of 55 mm.

As this embodiment is intended to be moulded in plastic, the extreme tips of the stimulator 50 can be given rounded edges, which are not easily provided when a stimulator is machined from wood. Thus, the top edges indicated at 80, and the vertical edges indicated at 82 can each have a radius of 0.25 mm. The bottom edge of each minimum profile, indicated at 84 in FIG. 7 is shown with a sharp of square corner. It can alternatively similarly be rounded to a radius comparable with that indicated at 80,82.

The top of the middle portion 56 can have a radius of 90 mm. Each of the ribs 62·can have a radius of 0.25 mm in cross-section, and here they are spaced at 2½ mm intervals. Also, instead of ribs, the stimulator can be left rough in the middle, this roughness being left by the moulding, and polished only at the ends.

The dimensions given above are for the particular embodiment shown. As for the first embodiment, it is to be appreciated that the dimensions are only exemplary. Again, a wide variety of dimensions could be employed, and below typical ranges are outlined.

Considering the first end portion 52, its length can vary in the range 0.10-30 mm. For its maximum profile 58, the height can vary in the range 3-6.25 mm, and its side radius in the range 10-30 mm. For the minimum profile 64, the radius of the sides can again vary in the range 10-30 mm, and its height can vary in the range 0.25-1.5 mm. For the second end portion 54, its maximum profile 60 can vary in height in the range 1.5-5.5 mm. The radius of its sides, and also the sides of the minimum profile 70 can vary in the range 10-40 mm. The height of the smallest profile 70 can vary in the range 0.25-1.5 mm. The length of the second end portion 54 can vary in the range 6.35-20 mm.

The overall length of this stimulator can vary in the range 45-75 mm.

For the various rounded edges and the ribs, the exact radius used is not critical, provided it is sufficiently round, so as to feel comfortable and not to injure a user. When choosing the radius, various factors, such as the hardness of the material. should be considered.

This second embodiment of the stimulator 50 is used in the same manner as the first embodiment as described above. Thus, for each space defined between two teeth and the adjacent gum, each end portion 52, 54 can be used in turn to clean it, and remove plaque etc from the teeth and gums, whilst stimulating the gums The use of a plastic, such as low density polyethylene, also provides another significant advantage. The wooden version is relatively rigid, and cannot be flexed. This makes it difficult to reach certain teeth, particularly the molars at the rear of the mouth. When plastic is used, the stimulator 50 is more flexible, and can be bent to reach awkward areas. Thus, if it is desired to use the first end portion 52 at the back of the mouth, then the first end portion 52 can be bent by as much as a right angle, approximately at the junction between the end portion 52 and the middle portion 56. This greatly facilitates insertion of the first end portion 52 between two molars at the back of the mouth. This applies whether the end portion 52 is inserted from the outside, ie between the cheek and the teeth, or from the inside. Provided suitable plastic is used, the stimulator 50 can be flexed and bent many times to reach all the teeth.

Unlike wood, plastic does not soften when wet, and does not wear so quickly. Consequently, one stimulator 50 can be used for a complete cleaning session, whereas for known wooden stimulators, one requires 2, or even 3 or more stimulators, to effect a complete cleaning of the teeth.

Finally, it is to be emphasized that, although the first embodiment is described primarily for stimulators formed from wood and the second embodiment has been described primarily with reference to stimulators formed from plastic, either embodiment can be made from wood or plastic, or other suitable material. Where wood is used, the stimulators are preferably formed in batches, as described, and packaged in batches or sets. For plastic, the stimulators are preferably moulded individually, and packaged loose.

Also, the stimulators, whether formed in wood or plastic, can be given a flavour. For example, they can be flavoured with mint or menthol. Additionally, they can be coloured, and this colouring preferably corresponds to the flavouring, in accordance with current associations between flavour and colour. Thus, for a mint flavour, the stimulators could be coloured green or white.

Moulding in plastic has another advantage over machining from wood. Where the stimulator is machined, the profile of the ends is set by the cutter profile. For a moulded stimulator, at each end, the profile can vary along the length of the end section.

I claim:

1. An interdental stimulator comprising an elongate member for insertion between adjacent teeth, the elongate member having a generally triangular profile and having first and second end portions, which taper down to respective first and second ends of small cross-section, with the first end portion in cross-section having a height to width ratio greater than the height to width ratio of the cross-section of the second end portion, and with the cross-section of each of the first and second end portions being of uniform shape along the length thereof.

2. A interdental stimulator as claimed in claim 1, wherein the stimulator is symmetrical about a vertical plane containing its axis.

3. An interdental stimulator as claimed in claim 1 or 2, wherein the cross-section of the first and second end portions is an isosceles triangle.

4. A stimulator as claimed in claim 1, wherein sides of the first and second end portions are rounded, as viewed in section.

5. A stimulator as claimed in claim 4, wherein the first and second end portions have rounded sides that are convex.

6. A stimulator as claimed in claim 1, 4 or 5, wherein an upper ridge extends the length of the stimulator, and is generally rounded as viewed in section.

7. A stimulator as claimed in claim 1, which includes a central portion, between the first and second end portions.

8. A stimulator as claimed in claim 7, wherein the central portion includes a transition section between the first and second end portions.

9. A stimulator as claimed in claim 8, wherein the central portion includes a first portion having a cross-section corresponding to the greatest cross-section of the first end portion, and located between the first end portion and the transition section.

10. A stimulator as claimed in claim 8 or 9, which further includes a second section having a cross-section corresponding to the greatest cross-section of the second end portion, and located between the transition section and the second end portion.

11. A stimulator as claimed in claim 8, wherein the transition section has a lower profile corresponding to the first end portion and an upper profile corresponding to the second end portion, with shallow side ridges dividing said lower and upper profiles.

12. A stimulator as claimed in claim 8, wherein the central portion includes flat, vertical lower side surfaces.

13. A stimulator as claimed in claim 8 wherein the sides of each of the first and second end portions are rounded as viewed in section 14. A stimulator as claimed in claim 13 wherein the sides of the first and second end portions are convex.

15. A stimulator as claimed in claim 14 wherein the central portion has an upper ridge which curves convexly, when viewed from the side.

16. A stimulator as claimed in claim 1, wherein each of the first and second end portions has a rounded upper ridge.

17. A stimulator as claimed in claim 16, wherein the upper ridges of the first and second end portions are both convex.

18. A stimulator as claimed in claim 1, which is formed from a plastic.

19. An interdental stimulator comprising an elongate member for insertion between adjacent teeth, the elongate member comprising: a first end portion, which tapers down to a first end of small cross-section; a second end portion, which tapers down to a second end of small cross-section, with the height to width ratio of the first end portion being greater than the height to width ratio of the second end portion; a central portion between the first and second end portions, which central portion includes a transition section; and a series of ribs spaced along the elongate member; wherein the sides of the first and second end portions are convex when viewed in cross-section.

20. A stimulator as claimed in claim 19, wherein the central portion includes a series of ribs spaced therealong, each rib extending across both sides of the central portion.

21. A stimulator as claimed in claim 19, wherein tips of the first and second end portiosn are rounded.

22. A stimulator as claimed in claim 19, which is formed from a plastic.

23. A stimulator as claimed in claim 19 which is formed from a plastic which is impregnated with a flavouring agent.

24. An interdental stimulator comprising an elongate member for insertion between adjacent teeth, the elongate member having a gnerally triangular profile and having first and second end portions, which taper down to respective first and second ends of small cross-section, with the first end portion in cross-section having a hiehgt ot width ratio greater than the height to width ratio of the cross-section of the second end portion, and with each of the first and second end protions terminating in a truncated tip.

25. An interdental stimulator as claimed in claim 1 or 24, which includes a central portion between the first and second end portions, and wherein the total length of the first and second end portions is comparable to, or greater than, the length of the central portion.

26. A stimulator as claimed in claim 1, 24 or 25 wherein each of the first and second end portions has an upper ridge that is straight and inclined.

27. A set fo stimulators, each of which comprises an elongate member for isnertion between the teeth, the elongate member having a generally triangular profile and having first and second end portions, which taper down to respective first and second end portions of small cross-section, with the cross-section of the first end portion having a height to width ratio greater than the height to width ratio of the second end portion and with the cross-section of each of the first and second end portions being of uniform shape along the length thereof, and a central portion between the first and second end portions which central portion inludes vertical lower side surfaces; and wherein the stimulators are arranged side by side in a row, with the stimulators being adjacent and continuous with one another at their vertical lower side surfaces.

28. a method of forming a stimulator comprising an elongate member for insertion between adjacent teeth, the elongate member having a generally triangular profile and having first and second end portions, which taper down to respective first and second end protions of small cross-section, with the first end portion in cross-section having a height to width ratio greater than the height of width ratio of the cross-section of the second end portion and with the cross-section of each of the first and second end portions being of uniform shape along the length thereof; the method comprising passing a first cutter having a first profile corresponding to the first end portion along an elongated member and along a first path such as to form the tapered profile for the first end portion of the elongated member, and passing a second cutter having a second profile corresponding to the second end portion of the elongated member and along a second path such as to form the tapered profile for the second end portion.

29. A method of forming a plurality of interdental stimulators, each moulded from plastic and comprising an elongate member for insertion between adjacent teeth, the elongate member having a generally triangular profile and hasving first and second end protions, which taper down to respective first and second end portions of small cross-sections, with the first end portion in cross-section having a height to width ratio greater than the height to width ratio of the cross-section of the second end portion and with the cross-section of each of the first and second end portions being of uniform shape along the length thereof, and a central portion between the first and second end portions, the stimulator having convex sides; the method comprising forming the stimulators in a common mould having a plurality of individual stimulator cavities with the stimulators joined to one another, and separating the individual stimulators.

* * * * *